(12) United States Patent
Shah et al.

(10) Patent No.: US 8,337,564 B2
(45) Date of Patent: Dec. 25, 2012

(54) TOTAL KNEE REPLACEMENT PROSTHESIS

(75) Inventors: Asit Shah, Ridgewood, NJ (US); Murali Jasti, Weston, MA (US)

(73) Assignee: Maxx Orthopedics, Inc., Plymouth Meeting, PA (US)

( * ) Notice: Subject to any disclaimer, the term of this patent is extended or adjusted under 35 U.S.C. 154(b) by 135 days.

(21) Appl. No.: 12/388,182

(22) Filed: Feb. 18, 2009

(65) Prior Publication Data

US 2009/0319048 A1 Dec. 24, 2009

Related U.S. Application Data

(60) Provisional application No. 61/029,457, filed on Feb. 18, 2008, provisional application No. 61/029,438, filed on Feb. 18, 2008.

(51) Int. Cl.
*A61F 2/38* (2006.01)
(52) U.S. Cl. .................... 623/20.27; 623/20.15
(58) Field of Classification Search .... 623/20.14–20.36, 623/16.11–17.16, 18.11, 19.11–19.14, 21.11–21.19
See application file for complete search history.

(56) References Cited

U.S. PATENT DOCUMENTS

| | | | | |
|---|---|---|---|---|
| 3,949,428 A | * | 4/1976 | Cavendish et al. | 623/20.3 |
| 3,996,624 A | * | 12/1976 | Noiles | 623/20.24 |
| 4,822,365 A | * | 4/1989 | Walker et al. | 128/898 |
| 5,080,675 A | * | 1/1992 | Lawes et al. | 623/20.33 |
| 5,219,362 A | * | 6/1993 | Tuke et al. | 623/20.31 |
| 5,246,459 A | * | 9/1993 | Elias | 623/20.34 |
| 5,556,432 A | * | 9/1996 | Kubein-Meesenburg et al. | 623/20.21 |
| 5,683,467 A | * | 11/1997 | Pappas | 623/20.32 |
| 5,702,459 A | * | 12/1997 | Hummer et al. | 623/20.18 |
| 5,824,101 A | * | 10/1998 | Pappas | 623/20.33 |
| 5,879,390 A | * | 3/1999 | Kubein-Meesenburg et al. | 623/20.21 |
| 6,190,415 B1 | * | 2/2001 | Cooke et al. | 623/20.33 |
| 6,679,917 B2 | * | 1/2004 | Ek | 623/20.14 |
| 6,911,100 B1 | * | 6/2005 | Gibbs et al. | 148/668 |
| 7,105,027 B2 | * | 9/2006 | Lipman et al. | 623/20.29 |
| 7,422,605 B2 | * | 9/2008 | Burstein et al. | 623/20.33 |
| 7,618,462 B2 | * | 11/2009 | Ek | 623/20.14 |
| 7,678,151 B2 | * | 3/2010 | Ek | 623/20.14 |
| 7,708,782 B2 | * | 5/2010 | Burstein et al. | 623/20.33 |
| 2002/0147498 A1 | * | 10/2002 | Tallarida et al. | 623/20.14 |
| 2003/0060887 A1 | * | 3/2003 | Ek | 623/20.14 |
| 2003/0225456 A1 | * | 12/2003 | Ek | 623/20.14 |
| 2004/0006394 A1 | * | 1/2004 | Lipman et al. | 623/20.29 |
| 2004/0148030 A1 | * | 7/2004 | Ek | 623/20.14 |
| 2005/0027365 A1 | * | 2/2005 | Burstein et al. | 623/20.32 |
| 2005/0043809 A1 | * | 2/2005 | Ryd | 623/20.32 |
| 2005/0278025 A1 | * | 12/2005 | Ku et al. | 623/14.12 |
| 2006/0195195 A1 | * | 8/2006 | Burstein et al. | 623/20.33 |
| 2008/0300690 A1 | * | 12/2008 | Burstein et al. | 623/20.29 |
| 2008/0319512 A1 | * | 12/2008 | Sherman | 607/61 |

(Continued)

*Primary Examiner* — Alvin J Stewart
(74) *Attorney, Agent, or Firm* — Joseph M. Konieczny, Sr.; Ryder, Lu, Mazzeo & Konieczny LLC

(57) ABSTRACT

A knee replacement prosthesis comprising a femoral component and a tibial component that enable anterior-posterior translation of the femur relative to the tibia and enable the tibia to rotate about its longitudinal axis during flexion of the knee. The femoral component connects to the distal end of a resected femur and includes medial and lateral condyles having distal, articulating surfaces, and a patellar flange having a patellar articulating surface. The tibial component connects to the proximal end of a resected tibia and includes a proximal bearing surface with medial and lateral concavities that articulate with the medial and lateral condyles. The articulating surfaces of the condyles and concavities are defined by sections of toroids.

38 Claims, 20 Drawing Sheets

U.S. PATENT DOCUMENTS

| | | | |
|---|---|---|---|
| 2009/0319048 A1* | 12/2009 | Shah et al. | 623/20.29 |
| 2009/0319049 A1* | 12/2009 | Shah et al. | 623/20.31 |
| 2010/0070045 A1* | 3/2010 | Ek | 623/20.14 |
| 2011/0087333 A1* | 4/2011 | Kellar et al. | 623/20.35 |
| 2011/0125275 A1* | 5/2011 | Lipman et al. | 623/20.11 |
| 2011/0125279 A1* | 5/2011 | Lipman et al. | 623/20.27 |
| 2011/0218635 A1* | 9/2011 | Amis et al. | 623/20.18 |

* cited by examiner

TOTAL KNEE REPLACEMENT PROSTHESIS

RELATED APPLICATIONS

This is a nonprovisional application claiming priority to U.S. provisional application No. 61/029,457 filed Feb. 18, 2008 entitled Total Knee Replacement Prosthesis, incorporated herein by reference, and U.S. provisional application No. 61/029,438 filed Feb. 18, 2008 entitled Total Knee Replacement Prosthesis with High Order NURBS Surfaces, incorporated herein by reference.

FIELD OF THE INVENTION

The present invention relates to a total knee replacement prosthesis, in particular, a prosthetic knee implant having articulating surfaces defined by toroidal surfaces that more accurately mimic the function and movement of the natural knee.

BACKGROUND OF THE INVENTION

While seemingly simple to the casual observer, the human knee articulates along a complex path. As the knee is flexed, the tibia obviously rotates (flexes) about a coronal axis relative to the femur. However, the femur also translates posteriorly on the tibia and the tibia also rotates about its longitudinal axis. Further, as the knee is flexed, the patella is drawn medially. The complex articulation path of the human knee is dictated primarily by the geometry of the distal femur and proximal tibia. For example, the medial femoral condyle is shorter and spherical in shape, while the lateral femoral condyle is longer and ellipsoidal in shape. The medial tibial condyle is concave whereas the lateral condyle is convex.

The complex path of articulation of the human knee is also dictated by the arrangements of ligaments surrounding and connecting the distal femur and proximal tibia. The human knee is complemented by two collateral ligaments, one on the lateral side of the joint and the other on the medial side thereof. Each ligament is attached to the tibia and the femur. The attachment points to the femur are approximately on the axis of the arc along which the other end of the tibia moves and the knee flexes. The collateral ligaments provide stability to the knee in varus and valgus stresses.

The human knee further includes two cruciate ligaments in the middle of the knee joint. One cruciate ligament is attached to the posterior margin of the tibia, while the other is attached towards the anterior margin of the tibia. Both ligaments are attached to the femur in the notch between the condyles approximately on the axis of the collateral ligaments. The cruciate ligaments provide stability in the anterior and posterior direction, and also allow the knee to rotate axially, i.e., about its longitudinal axis. Thus, as the knee is flexed, the tibia undergoes internal rotation about its longitudinal axis.

Known total knee replacement prostheses generally consist of a femoral component and a tibial component, which are attached to the resected surfaces of the distal femur and the proximal tibia, respectively, either by pressure fitting or by adhering with polymethyl methacrylate bone cement. Each component includes a pair of condylar surfaces that compliment one another and allow the components to articulate relative to one another. The geometry of the complimenting condylar surfaces determines the complexity of movement and degrees of freedom, namely, whether the components can flex, translate and/or rotate relative to one another. The femoral component also includes a patellar flange, which articulates either with the natural patella or an artificial patellar component. The patellar flange provides the lever arm for the quadriceps muscle.

Known total knee prostheses do not accurately replicate the condylar surfaces of the human knee. For example, the femoral condylar surfaces of known prostheses are generally convex and rounded in the medial-lateral direction and anterior-posterior direction. The radius of curvature in the anterior-posterior direction is larger than the radius of curvature in the medial-lateral direction. Generally, the arc center of the sagital curvature of the distal and posterior aspects of condyles are centered on the axis joining the medial and lateral epicondyles, so that the tension in the collateral ligaments, which attach to the epicondyles, remains nearly constant in flexion and extension. The tibial surfaces are generally concave and dish-shaped with their major axis aligned in the sagital plane. The sagital and coronal radii of the tibial condyles are greater than the sagital and coronal radii of the femoral condyles, which provides some degree of rotational laxity. Likewise, the patellar flange on the femur is concave and oriented from superior to inferior direction with a radius of coronal curvature greater than that of the dome shaped patella.

The design of many prior art total knee replacement components ignore the complex rotational movements of the natural knee in favor of a simple hinge design, which allows only pivotal rotation about a single horizontal axis. Such simple designs have largely been abandoned because of high loosening rates associated with the high rotational stresses placed on the prosthetic components. Other prior art knee prostheses attempt to more closely mimic the motion path of the natural knee. However, these prostheses do not accurately replicate the natural motion path of the human knee and have other manufacturing and durability limitations.

Many of the prior art knee replacement prostheses are modeled using a single geometry such as circles, arcs, lines, planes, spheres, and cylinders, which have well defined lengths and radii of curvature. However, the complex motion path of the human knee can not be replicated using simple geometries. Prostheses modeled using simple geometries produce unnatural motion, undue tension and pain in the ligaments, and increased wear and loosening of the prosthetic components. Therefore, it would be desirable to provide a knee replacement prosthesis with more complex articulating surfaces, which replicate the motion of the natural knee by allowing femoral translation and tibial rotation as the knee is flexed, and which is easy and inexpensive to manufacture.

SUMMARY OF THE INVENTION

The invention provides a total knee replacement prosthesis that mimics the motion of the natural knee by allowing femoral translation and tibial rotation as the knee is flexed. The novel prosthesis comprises a femoral component that articulates with a tibial component and the natural or prosthetic patella. The articulating surfaces of the components are designed with toroidal surfaces that allow flexion, translation and rotation under physiologic load to replicate the motion path of the natural knee.

In one embodiment, the knee replacement prosthesis comprises a femoral component that connects to the distal end of a resected femur and a tibial component that connects to the proximal end of a resected tibia. The femoral component includes medial and lateral condyles having a distal, articulating surface with a toroidal anterior surface and a toroidal posterior surface with major and minor radii of curvature. The femoral component also includes a patellar flange having an articulating patellar surface. The tibial component includes a proximal bearing surface with medial and lateral concavities that articulate with the medial and lateral condyles. The concavities have a toroidal anterior surface and a toroidal posterior surface with major and minor radii of curvature. The anterior and posterior surfaces of each concavity are blended smoothly together, and are preferably fitted with a patch surface that articulates with the condyles.

The condylar surfaces and concavities are substantially defined by toroidal surfaces (sections of toroids), which enable anterior-posterior translation of the femur relative to the tibia, and which enable the tibia to rotate about its longitudinal axis during flexion of the knee. The toroidal surfaces of the prosthesis are designed such that under weight bearing and muscular loads, the movement of the natural knee is mimicked.

In a preferred embodiment, the tibia has minimal axial rotation, less than 10 degrees, as the knee is initially flexed from full extension to an intermediate position of about 30 degrees. After continued flexion past the intermediate position, the tibia then rotates axially to full flexion. When the prosthesis is fully flexed, the tibia preferably rotates axially more than about 10 degrees, preferably more than about 15 degrees, and more preferably up to about 20 degrees.

The prosthesis enables translation of the femur relative to the tibial. The condyles translate posteriorly in the concavities during flexion and translate anteriorly during extension. In a preferred embodiment, the posterior/anterior translation is about 1-2 millimeters during full flexion.

The prosthesis also enables a high degree of flexion. In a preferred embodiment, the posterior portion of each condyle is shaped to allow flexion greater than 110 degrees, preferably greater than 130 degrees, and more preferably up to about 155 degrees.

The major radius of curvature of each of the condylar anterior surface and the condylar posterior surface is oriented in the sagital plane, and the minor radius of curvature of each surface is oriented generally in the coronal plane. The major radii of curvature of the anterior surface and posterior surface of each condyle may be equal or unequal, and the minor radii of curvature of the surfaces are preferably equal. The major radius of curvature of each condylar surface is preferably centered on the axis joining the medial and lateral epicondyles of the femur.

The major radius of curvature of the anterior surface of each concavity is oriented in the sagital plane, and the minor radius of curvature is oriented generally in the coronal plane. The major radius of curvature of the posterior surface of each concavity is oriented in the transverse plane, and the minor radius of curvature is oriented generally in the coronal plane. The medial and lateral concavities may share a single center of rotation for each the major radius of curvature or have a different center for the major radius of curvature. Preferably, the major radii of curvature of the anterior and posterior surfaces of each concavity are unequal and the minor radii of curvature are equal. The minor radius of curvature of the condylar surfaces is equal to or smaller than the minor radius of curvature of the anterior and posterior surfaces of the concavities.

In an asymmetric embodiment, each of the anterior surfaces of the medial and lateral condyles has a different major radius of curvature, and each of the posterior surfaces of the medial and lateral condyles has a different major radius of curvature. In this embodiment, each of the anterior and posterior surfaces of the medial and lateral condyles has the same minor radius of curvature. Each of the anterior surfaces of the medial and lateral concavities also has a different major radius of curvature, and each of the posterior surfaces of the medial and lateral concavities has a different major radius of curvature.

In another embodiment, each of the condylar anterior surfaces and posterior surfaces has multiple major radii of curvature in the sagital plane. Each of the condylar anterior and posterior surfaces has the same minor radius of curvature. In this embodiment, each of the anterior surfaces of the concavities has multiple major radii of curvature in the sagital plane and each of the posterior surfaces has multiple major radii of curvature in the transverse plane. Each of the anterior and posterior surfaces of the concavities has the same minor radius of curvature.

The tibial component includes a base having distal and proximal surfaces, and a liner having a distal surface that engages the proximal surface of the base and a proximal surface forming the bearing surface that engages and articulates with the femoral component. The base comprises a base plate that rests on the tibial plateau, and a keel fixed to the distal surface of the plate that can be inserted into the proximal tibial medullary canal. Preferably, the distal surface of the base plate has a textured, roughened surface.

One embodiment of the prosthesis is designed for use when the posterior cruciate ligament is surgically removed. In this embodiment, the femoral component includes an asymmetric cam connecting the posterior ends of the condyles, and the tibial component includes a central, symmetric post intermediate the concavities. Anterior and posterior translation of the femoral component relative to the tibial component, as well as tibial axial rotation, is controlled by the cam and the central post. Contact between the cam and post occurs at knee flexion greater than about 30 degrees. The articular surfaces enable posterior femoral rotation and internal tibial rotation as the knee is flexed.

Another embodiment of the prosthesis is designed for use when the posterior cruciate ligament is retained. In this embodiment, the femoral component does not include the cam and the tibial component does not include the central post. Anterior and posterior translation of the femoral component relative to the tibial component, as well as tibial axial rotation, is controlled by the posterior cruciate ligament. The articular surfaces enable posterior femoral rotation and internal tibial rotation as the knee is flexed.

DETAILED DESCRIPTION OF PREFERRED EMBODIMENTS

Figure 1:
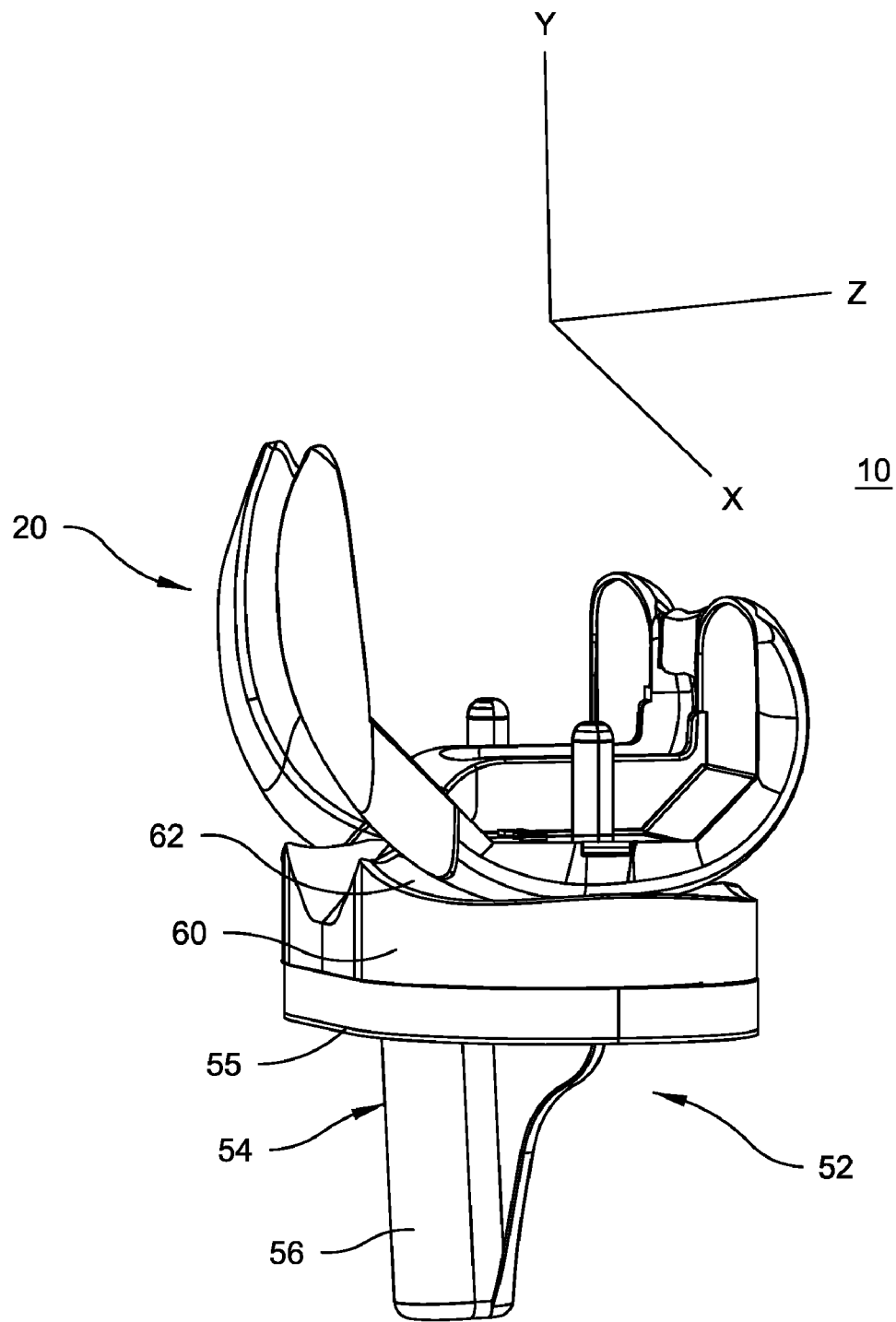
FIG. 1 is a perspective of a knee prosthesis in full extension in accordance with an embodiment of the invention.
Figure 2:
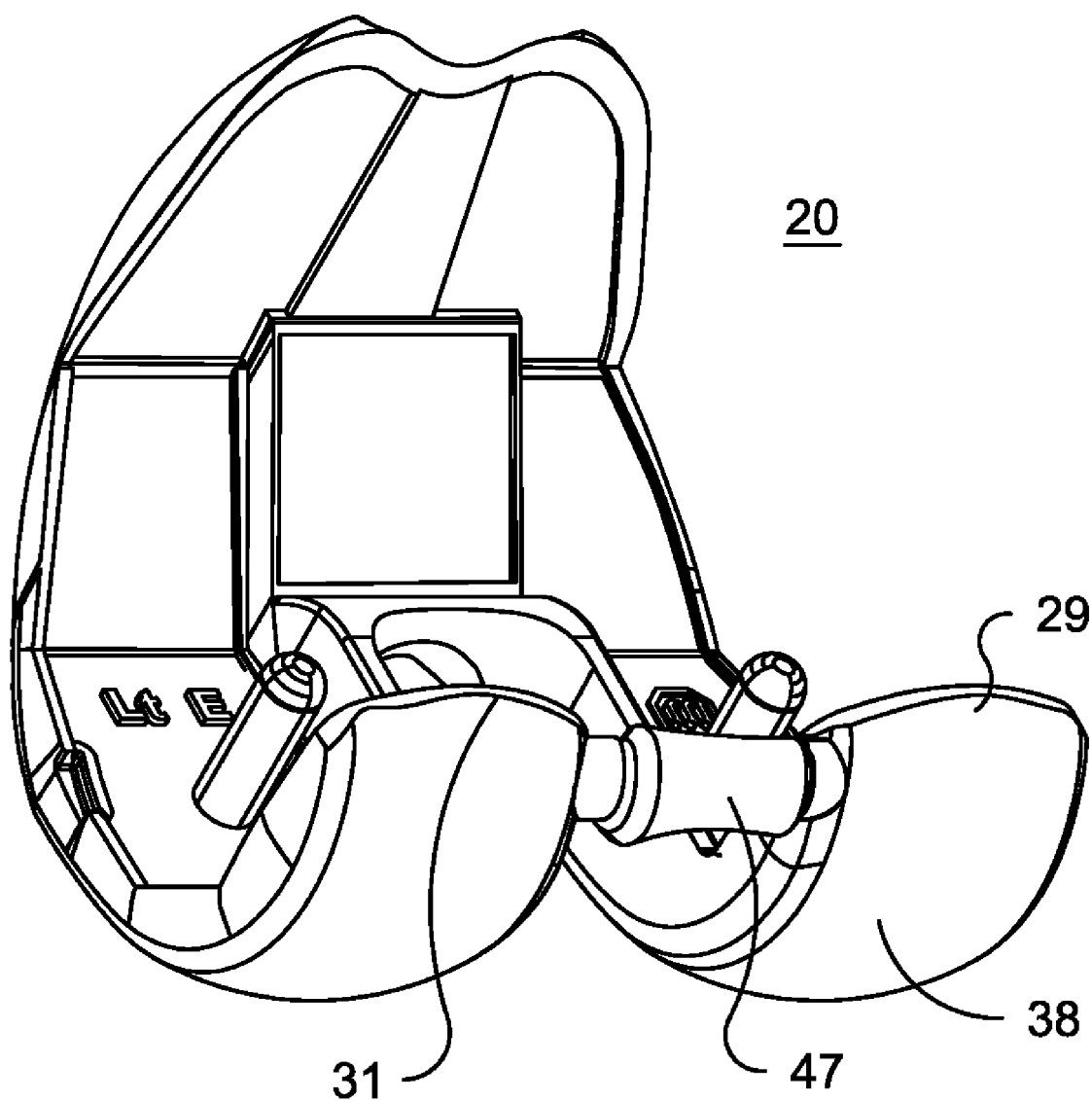
FIG. 2 is a perspective showing the proximal surface of the femoral component shown in FIG. 1.
Figure 3:
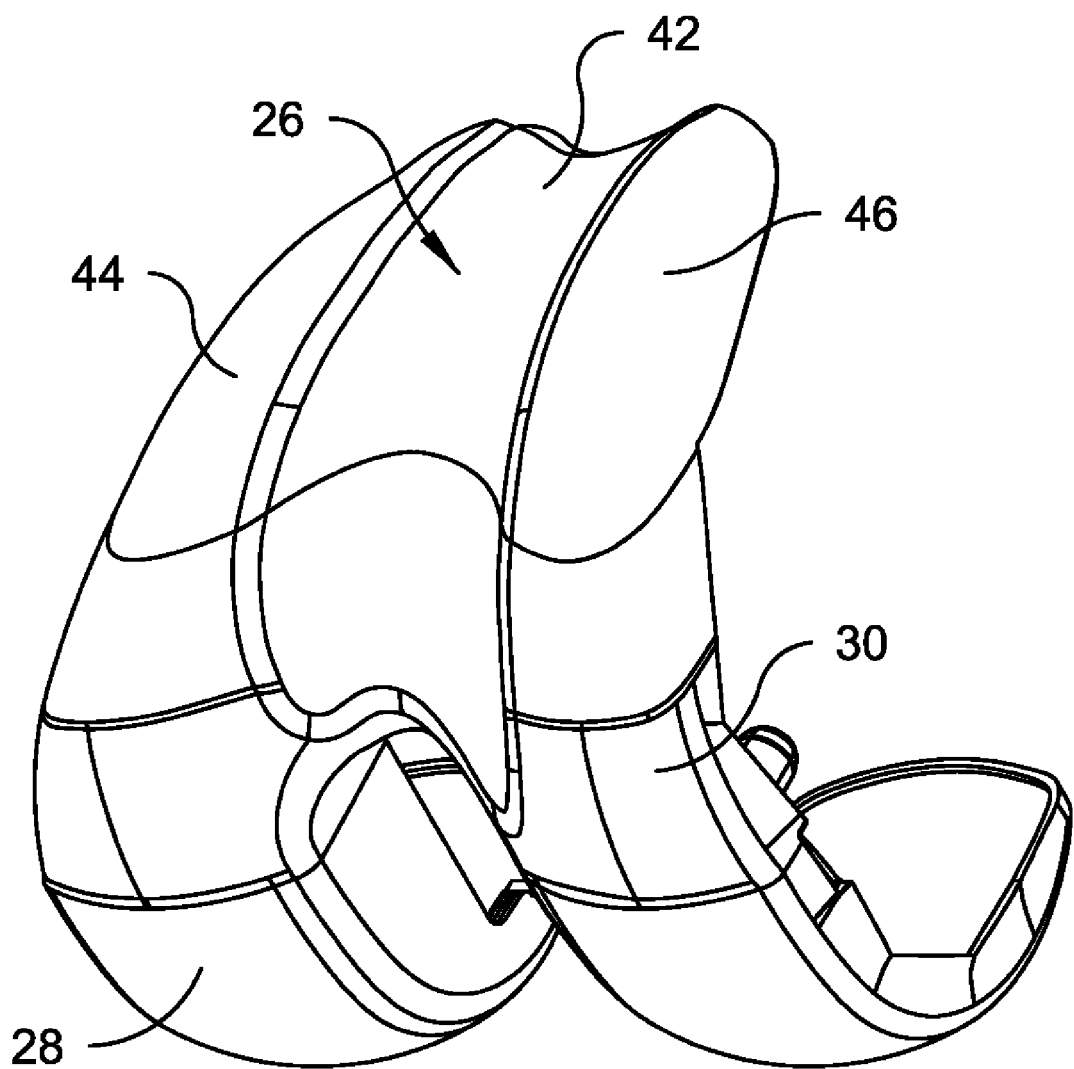
FIG. 3 is a perspective showing the patellar flange and anterior condylar portion of the femoral component shown in FIG. 1.
Figure 4:
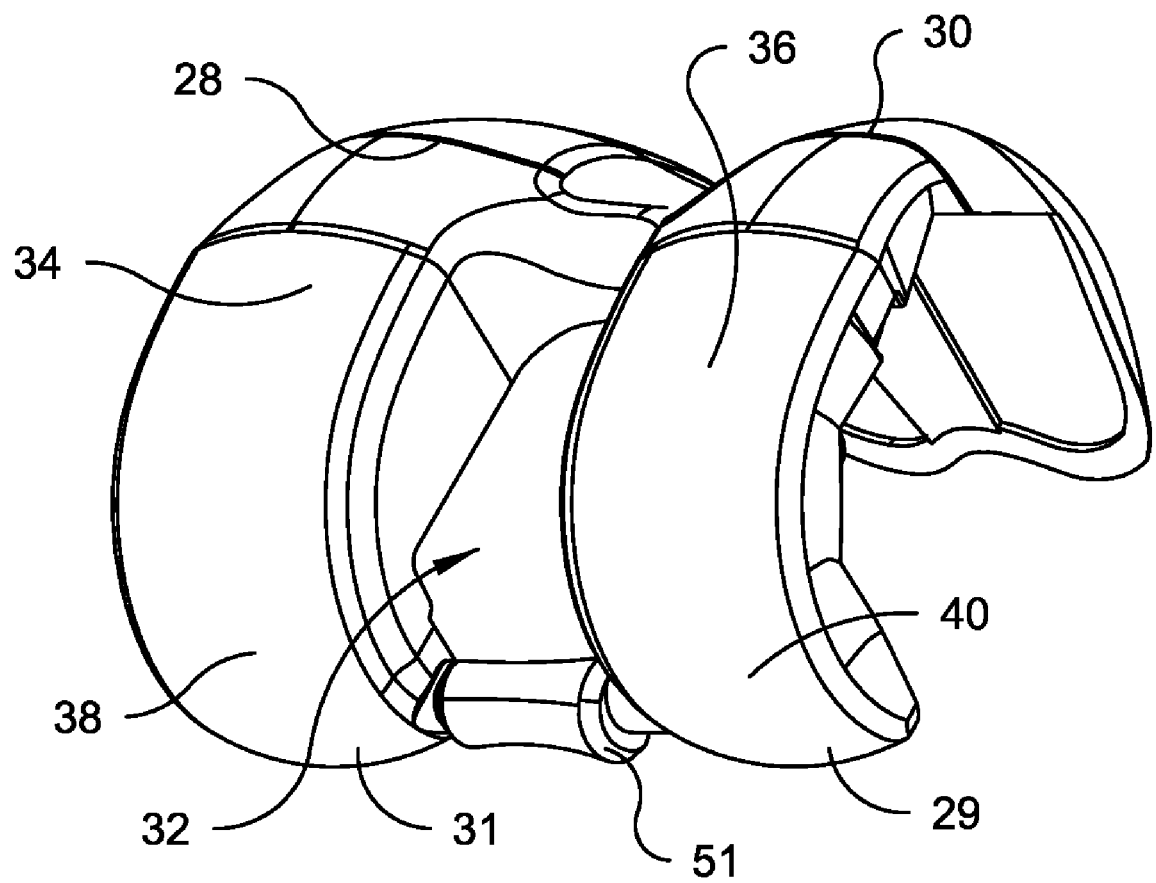
FIG. 4 is a perspective showing the anterior and posterior condylar portions of the femoral component shown in FIG. 1.

For the purpose of illustrating the invention, several embodiments of the invention are shown in the accompanying drawings. However, it should be understood by those of ordinary skill in the art that the invention is not limited to the precise arrangements and instrumentalities shown therein and described below. Throughout the specification, like reference numerals are used to designate like elements. Numerous changes and modifications within the spirit and scope of the invention will become apparent to those skilled in the art from this detailed description.

Unless otherwise defined, all technical and medical terms used herein in their various grammatical forms have the same meaning as commonly understood by one of ordinary skill in the art to which this invention belongs. The terms "anterior", "posterior", "proximal", "distal", "medial", "lateral", "sagittal", "coronal", and "transverse" are used herein with their conventional medical/anatomical meaning as defined, for example, in Dorland's Illustrated Medical Dictionary.

The term "toroid" refers to a surface generated by a closed curve rotating about, but not intersecting or containing, an axis ("major axis") in its own plane. The term "major radius" refers to the radius of rotation of the closed curve about the major axis. The major radius lies in a plane orthogonal to the major axis. The term "minor radius" refers to the radius of the closed curve. The minor radius may be larger than the major radius.

A knee replacement prosthesis in accordance with an embodiment of the invention is illustrated in FIGS. 1-14 and is designated generally by reference numeral 10. The prosthesis 10 includes a femoral component 20, constructed and designed to be fixed to the distal end of a resected femur, and a tibial component 52, constructed and designed to be fixed to the proximal end of a resected tibia. The components 20, 52 can be fixed to the femur and tibia, respectively, using conventional methods after conventional femoral and tibial resection. The tibial component 52 has a symmetrical design that can be used on either the left or right knee; however, the femoral component is asymmetrical and is illustrated in FIGS. 1-14 for installation on the left knee. A mirror image of the femoral component 20 will be used for installation on the right knee.

Referring to the coordinate axes shown in FIG. 1, the prosthesis 10 has a sagital plane oriented in the Y-Z plane, a coronal plane oriented in the X-Y plane, and a transverse plane oriented in the X-Z plane. When the prosthesis is implanted, the sagital, coronal, and transverse planes align with the conventional sagital, coronal, and transverse planes, respectively, of the patient.

The femoral component 20 has a medial condylar portion or condyle 22, a lateral condylar portion or condyle 24, and a patellar flange portion or flange 26, which bridges the anterior ends 28, 30 of the medial 22 and lateral 24 condyles, respectively. The medial 22 and lateral 24 condyles are arranged in substantially parallel relationship to each other and define an intercondylar notch 32 therebetween. As the prosthesis flexes, different sections of the curved condylar portions engage and articulate with the tibial component 52.

Figure 6:
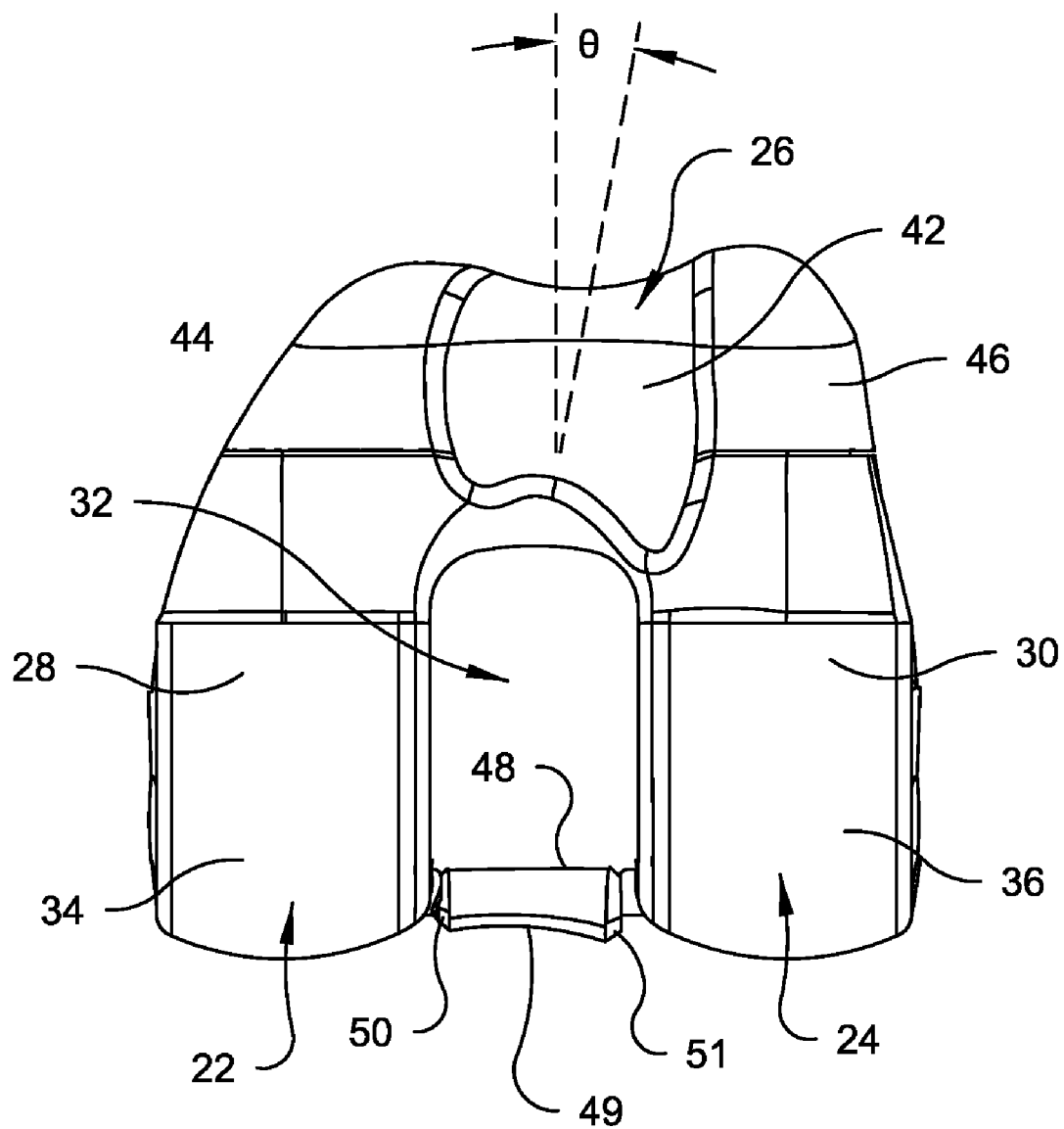
FIG. 6 is an anterior elevation showing the patellar flange and the anterior section of the condylar portion of the femoral component shown in FIG. 1.

The patellar flange 26 includes a patellar groove 42, which is flanked by a medial trochlear surface 44 and a lateral 46 trochlear surface. The patellar flange 26 is designed to articulate with either the natural patella or a prosthetic patellar component. As best seen in FIG. 6, the patellar flange widens inferiorly to accommodate the patella. The trochlear surfaces 44, 46 are elevated and transition smoothly into the patellar groove 42 to provide stability to the patella. Referring to FIG. 6, the patellar groove 42 extends upwardly and laterally at an angle theta ($\theta$) in the coronal plane in a curvilinear fashion along with the trochlear surfaces 44, 46 to provide optimal tracking and stability. In a preferred embodiment, the angle theta ($\theta$) is about 6 degrees. The patellar flange 26 also transitions smoothly with the condyles 22, 24. The patellar flange 26 is constructed by approximating the geometry of the distal anterior surface of a natural femur. As a result, the patellar flange 26 has natural tracking of the prosthetic or natural patella.

Each condyle 22, 24 generally comprises an anterior 34, 36 and posterior 38, 40 surface, which blend smoothly with each other without any abrupt transition. In the embodiment shown in FIGS. 1-14, the anterior and posterior surfaces are defined by sections of toroids. Each surface has its major radius lying substantially in the sagital plane. In a first embodiment, the major radius of curvature of the anterior surface 34, 36 is the same as the posterior surface 38, 40 on each condyle. Alternatively, the major radius of curvature of the condyles 22, 24 may decrease from front to back to mimic anatomic femoral rollback during high degrees of flexion. For example, the major radius of the anterior surface 34, 36 may be larger than the major radius of the posterior surface 38, 40. For an average knee, the major radius of curvature could be, for example, about 14 mm.

Alternatively, the major radius of the anterior and posterior surfaces may also reduce proceeding posteriorly. Each of the anterior and posterior condylar surfaces may be composed of multiple toroid sections having posteriorly reducing major radii of curvature. For example, the anterior surfaces 34, 36 may be composed of a first toroid section, and a second toroid section having a smaller major radius of curvature than the first toroid section. Similarly, the posterior surfaces 38, 40 may be composed of a first toroid section, and a second toroid section having a smaller major radius of curvature than the first toroid section. The reduction in radius is much greater in the posterior section than the anterior section. In particular, the surface proximate the posterior ends 29, 31 of the condyles 22, 24 has a major radius of curvature that is greatly reduced to enable a high degree of flexion, i.e., flexion greater than 110 degrees, preferably greater than 130 degrees, and more preferably up to about 155 degrees. Further, the small radii of the ends 29, 31 prevent edge loading of the condyles 29, 31 while maintaining contact between the condyles on the tibial liner 60.

The planar orientation of the minor radius of curvature varies. In a preferred embodiment, the condyles 22, 24 have a constant minor radius of curvature. However, the condylar surfaces could have varying minor radii of curvature. For an average knee, the minor radius of curvature could be, for example, about 20 mm.

Figure 7:
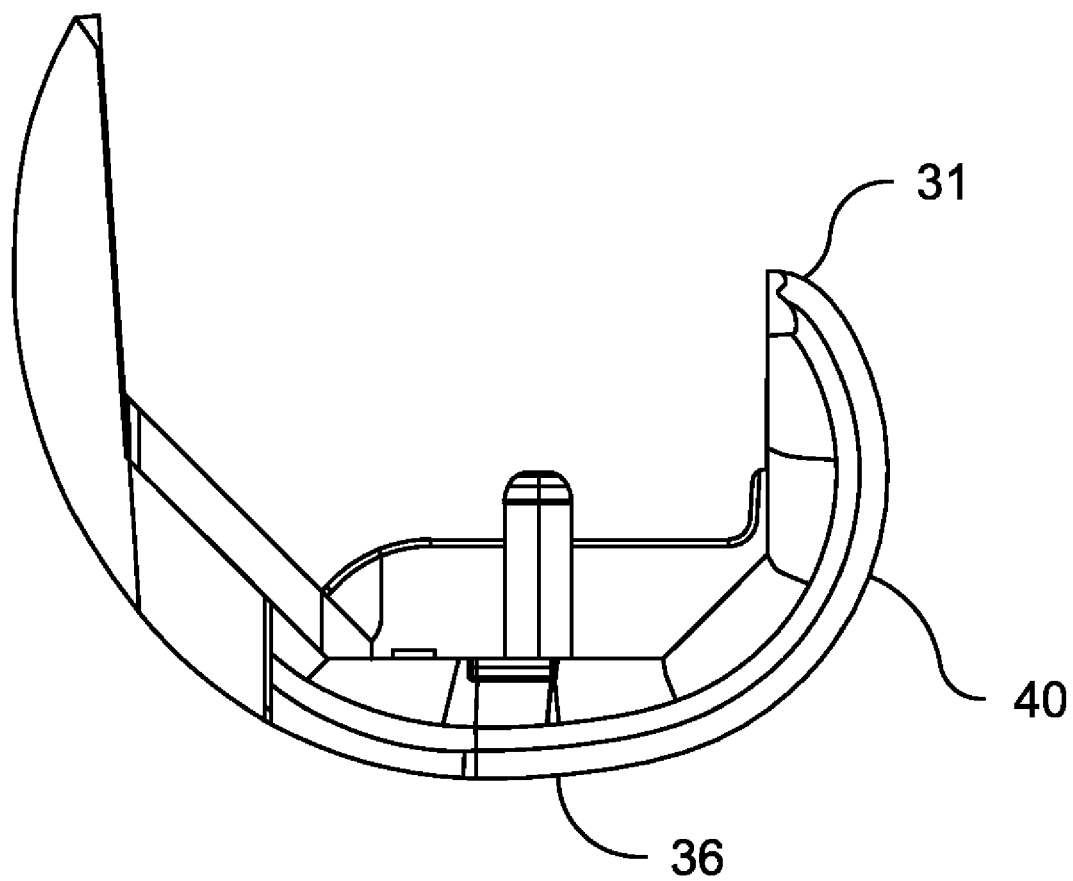
FIG. 7 is a lateral elevation of the femoral component shown in FIG. 1.
Figure 8:
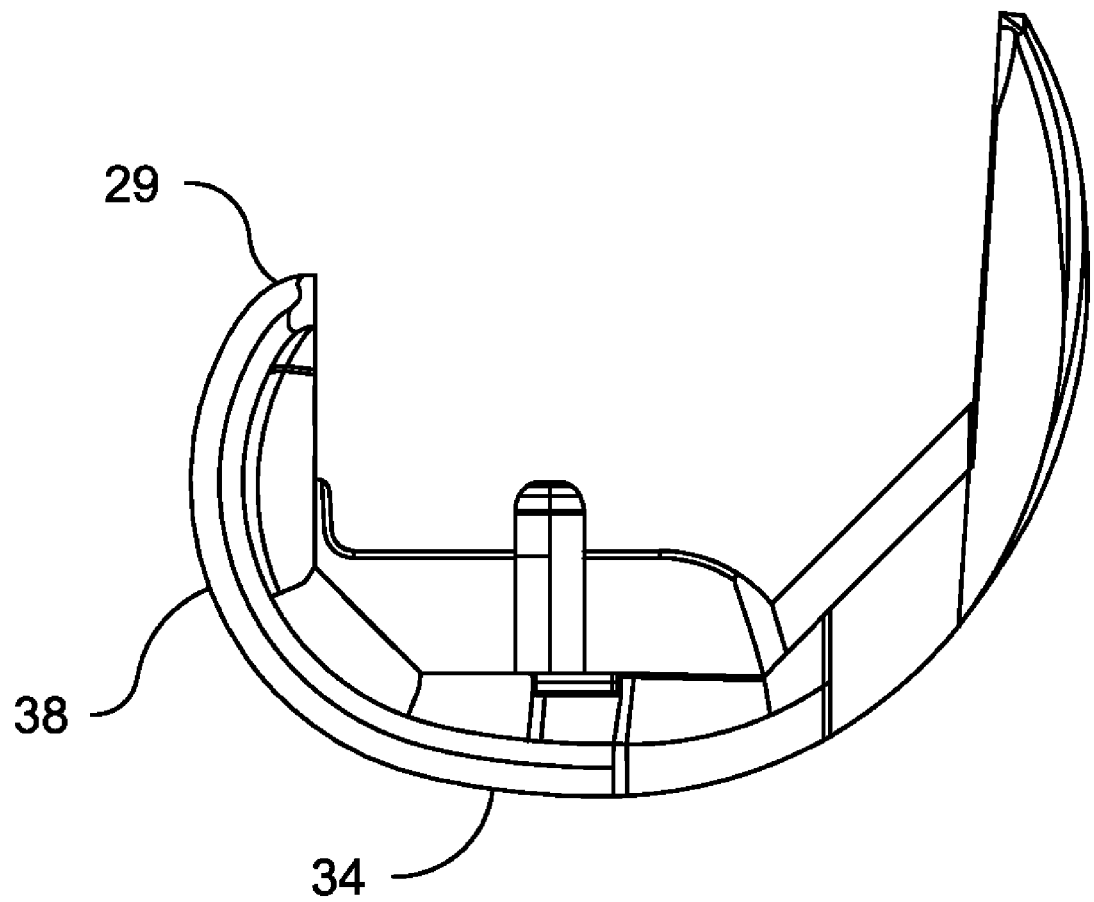
FIG. 8 is a medial elevation of the femoral component shown in FIG. 1.
Figure 9:
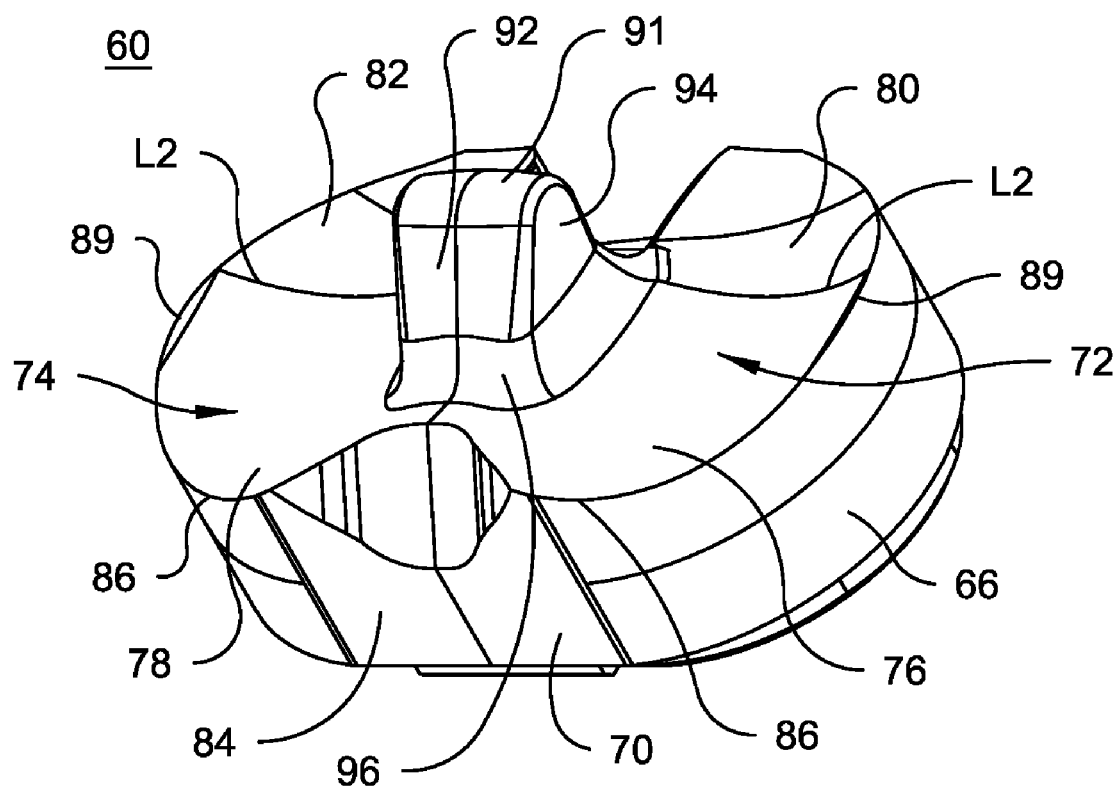
FIG. 9 is a perspective showing the anterior proximal surface of the tibial component liner of FIG. 1.
Figure 10:
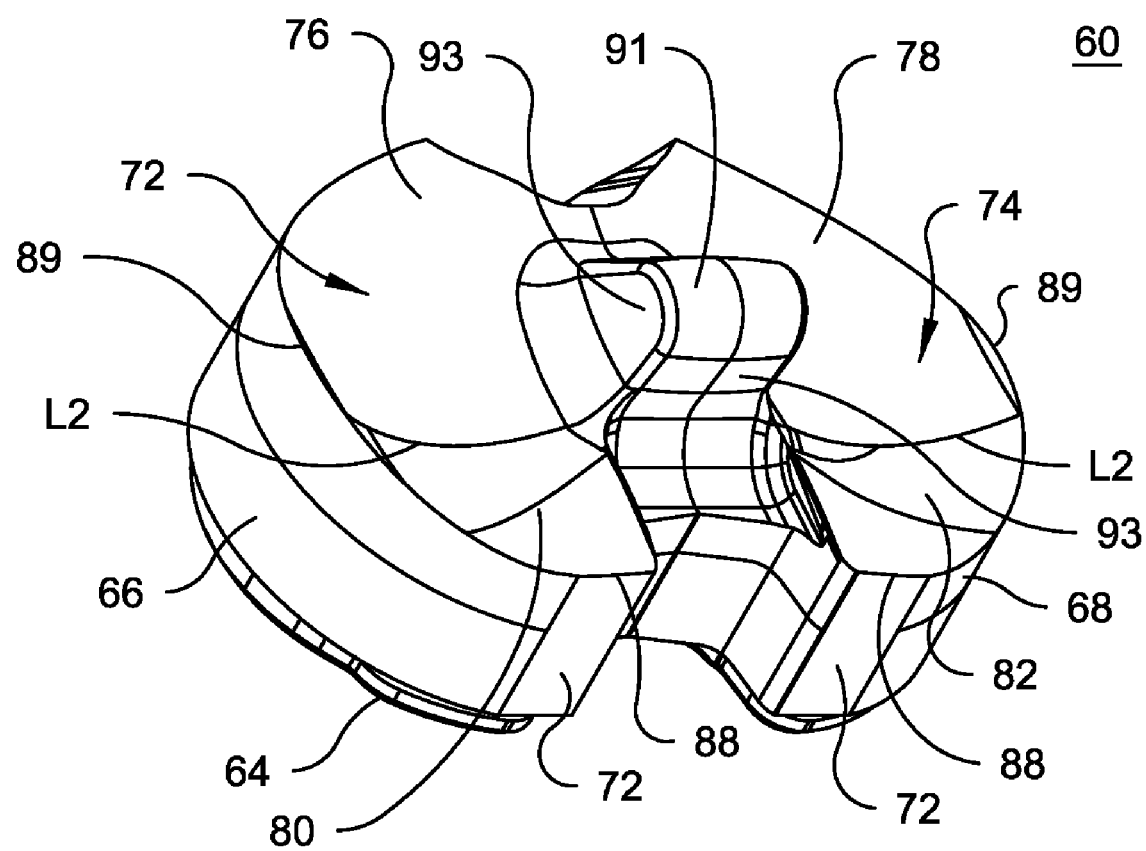
FIG. 10 is a perspective showing the posterior proximal surface of the tibial component of FIG. 1.
Figure 11:
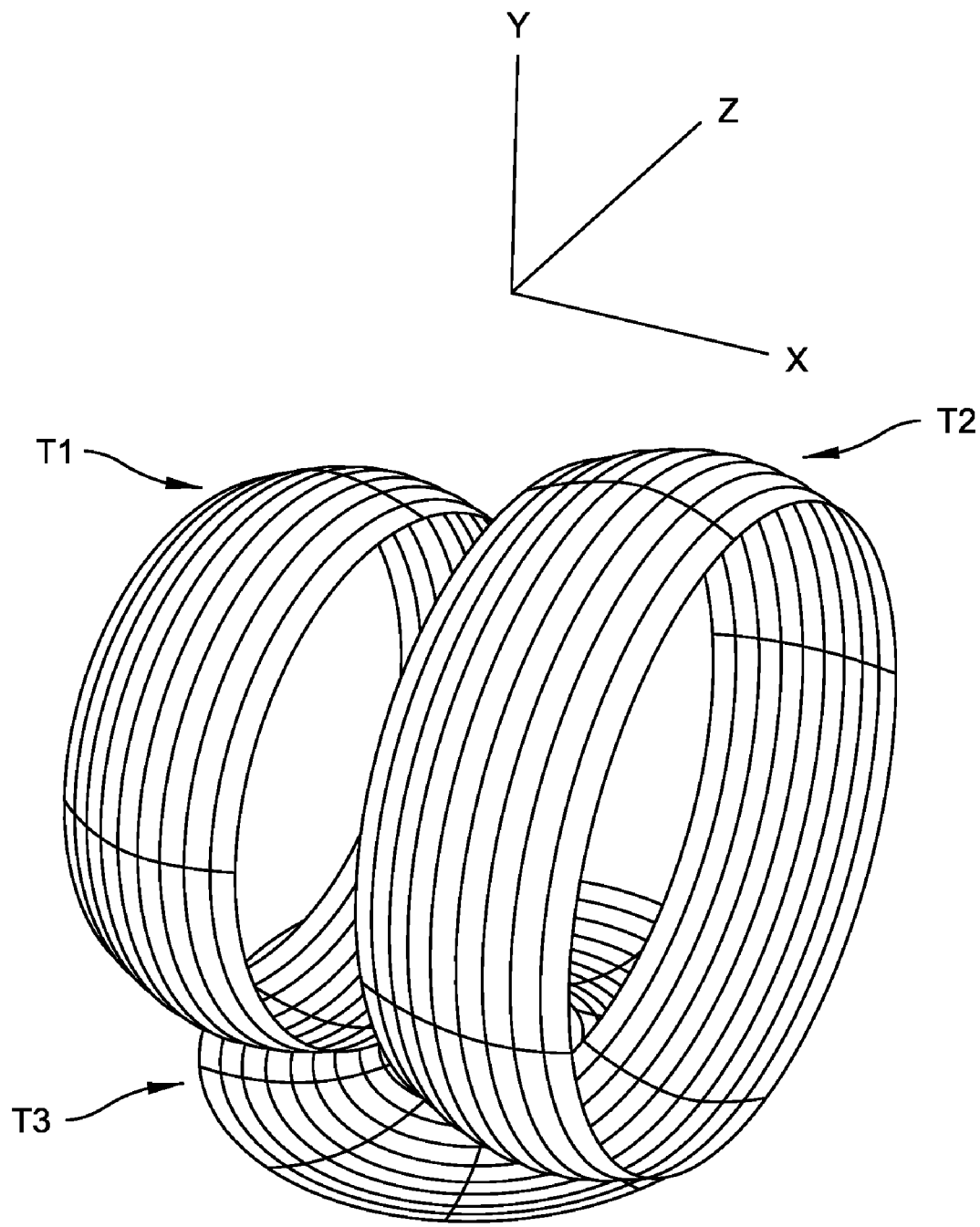
FIG. 11 is a graphical illustration of the orientation of the toroidal sections, along with coordinate axes relating the sagital, coronal and transverse planes of the prosthesis shown in FIG. 1.

In one embodiment, the lateral condyle 24 has larger major radii than the medial condyle 22 as seen in FIGS. 7 and 8 and graphically illustrated in FIG. 11. Despite being different, the major radii of each condyle 22, 24 are centered on the epicondylar axis of the knee. As described in greater detail below, the larger lateral condyle 24 helps the tibia to rotate axially as the femoral component translates posteriorly on the tibial component. However, it should be appreciated that the condyles 22, 24 could have the same major radii and still effect axial tibial rotation and femoral translation.

Figure 5:
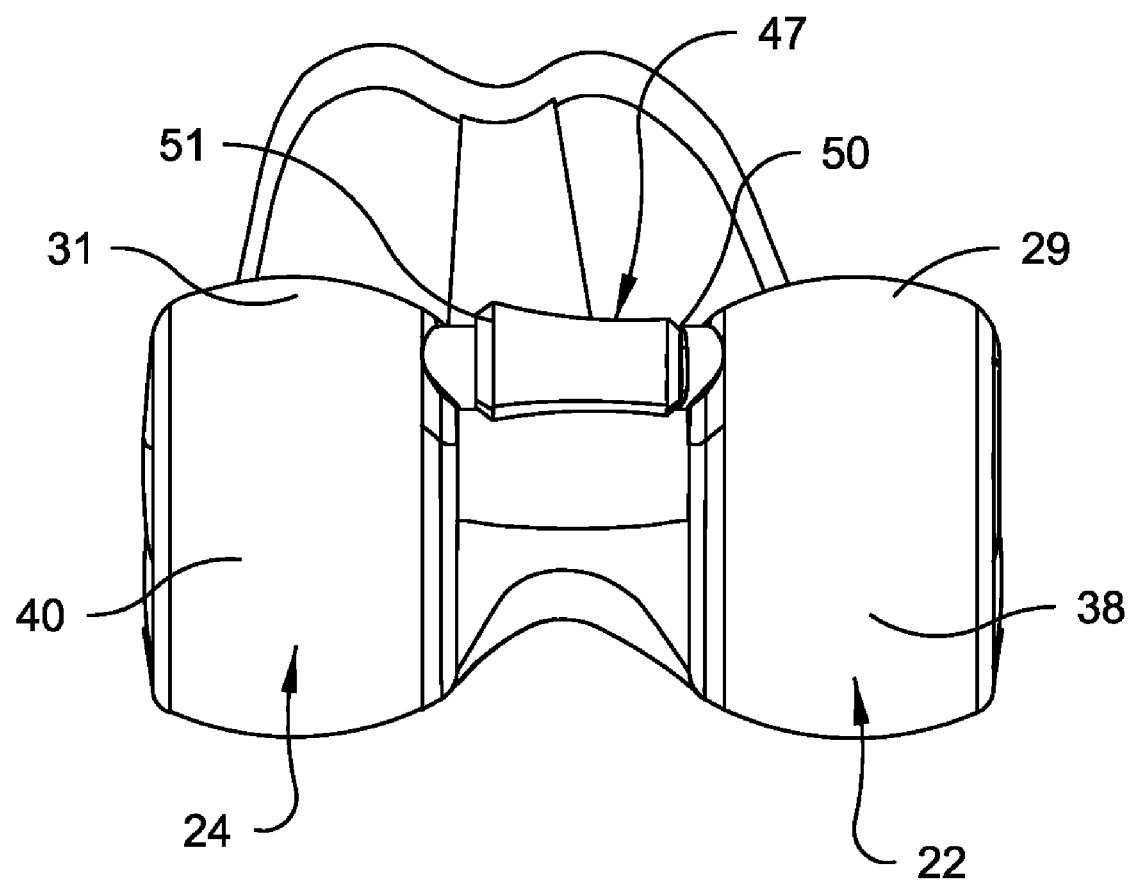
FIG. 5 is a posterior elevation showing the posterior section of the condylar portion of the femoral component shown in FIG. 1.

As best seen in FIGS. 5 and 6, a cam 47 bridges and connects the posterior ends 29, 31 of the medial 22 and lateral 24 condyles. Referring to FIG. 6, the cam 47 has a generally flat back surface 48 and a curved front bearing surface 49. The back surface 48 is oriented coplanar with the back (proximal) surface of the condyles 22, 24 and is flat to abut the resected surface of the distal femur as best seen in FIG. 1. As best seen in FIG. 5, the radius of curvature of the bearing surface 49 is larger at the lateral end 51 than the medial end 50. As described in greater detail below, the cam 47 engages a central post 90 on the tibial bearing liner 60 to provide stability and tibial rotation as the knee is flexed.

Referring to FIG. 1, the tibial component 52 generally comprises a tibial platform 54 and a liner 60. The tibial platform 54 has a base plate 55, which engages the distal surface 64 of the liner 60, and a stabilizing keel 56, which is inserted into the medullary canal of the tibia. The underside or distal surface of the base plate 55 has a textured, roughened surface that allows cement interdigitation during installation on the tibia.

The liner 60 has a proximal bearing surface 62, which articulates with the femoral component 20, and a distal surface 64, which abuts and is fixed to the tibial platform 52. The tibial component 50 also has a medial side 66, a lateral side 68, an anterior side 70, and a posterior side 72. The tibial component is generally symmetrical about a central sagital axis running anterior to posterior.

A medial concavity 72 and a lateral concavity 74 are formed in the medial and lateral sides of the proximal surface 62. The medial 72 and lateral 74 concavities engage the medial 22 and lateral 24 condyles of the femoral component 20 as the components articulate relative to one another. In general, the concavities 72, 74 are shallower than the depth of the femoral condyles 22, 24. Although described herein as concavities in a preferred embodiment, one or more of the condylar surface portions with which the femoral component articulates may be flat or even convex.

Each concavity 72, 74 generally comprises an anterior 76, 78 and posterior 80, 82 surface, respectively, which blend smoothly with each other without any abrupt transition. In the embodiment shown in FIGS. 1-14, the anterior and posterior surfaces are defined by sections of toroids, which blend together at an intermediate boundary. Each of the anterior surfaces 76, 78 has a major radius of curvature oriented substantially in the sagital plane. Each of the posterior surfaces 80, 82 has a major radius of curvature oriented substantially in the transverse plane. The posterior surfaces 80, 82 of the concavities 72, 74 curve posteriorly-inwardly toward the central sagital axis. The posterior surfaces 80, 82 rotate around a central point that is slightly posterior to the post 90. The centerline is continuous from the anterior concavity to the posterior concavity. The anterior 76, 78 and posterior 80, 82 surfaces have the same constant minor radius of curvature and share the same tangent intersection "L2". The minor radius of curvature of the posterior surface is maintained as it turns toward the central sagital axis. This construction allows the tibia to rotate about its longitudinal axis and translate posteriorly as the knee flexes.

Alternatively, each of the anterior and posterior surfaces of the concavities may be composed of multiple toroid sections having different major radii of curvature. For example, the anterior surfaces 76, 78 may be composed of a first toroid section and a second toroid section having a smaller major radius of curvature than the first toroid section. Similarly, the posterior surfaces 80, 82 may be composed of a first toroid section and a second toroid section having a smaller major radius of curvature than the first toroid section. In this embodiment, the anterior and posterior surfaces have the same minor radius of curvature.

The anterior and posterior concavities have a raised periphery at the anterior 86 and posterior 88 ends to contain and prevent dislocation of the femur from the tibia. The raised periphery also provides stability to the knee during flexion. As the condyles 22, 24 ride up the raised periphery of the concavities 72, 74, the collateral ligaments tighten and the knee becomes tighter.

The anterior concavities have lateral elevations 89, which contain the condyles 22, 24 so that the tibial component has little laxity during initial flexion and restricts tibial axial rotation. In contrast, the posterior concavities are designed without constraining lateral elevations and are designed to enable tibial axial rotation. This construction wherein the knee is substantially prevented or "locked" from rotating axially during initial flexion, but is able to rotate axially in flexed positions, is referred to as a screw home mechanism. In a preferred embodiment, tibial axial rotation is preferably substantially restricted to less than 10 degrees in the flexion range of full extension to an intermediate position of about 30 degrees. However, the toroidal surfaces can be shaped so that tibial axial rotation is substantially enabled at different intermediate positions of flexion. Additionally, the outer sides of the posterior surfaces 80, 82 are higher than the inner sides so that as the knee is flexed, axial tibial rotation relieves the tension on the collateral ligaments.

In the embodiment shown in FIGS. 1-14, the tibial component 60 includes a central post 90, which has a proximal surface 91, anterior surface 92, posterior surface 93, medial side surface 94, and lateral side surface 95. The anterior surface 92 of the central post 90 is tapered relative to the distal surface 64 to minimize impingement of the patella or a patellar implant in deep flexion. The base 96 of the anterior surface 92 may be tapered at a different angle to minimize impingement of the intercondylar notch 32 in hyperextension.

Figure 12:
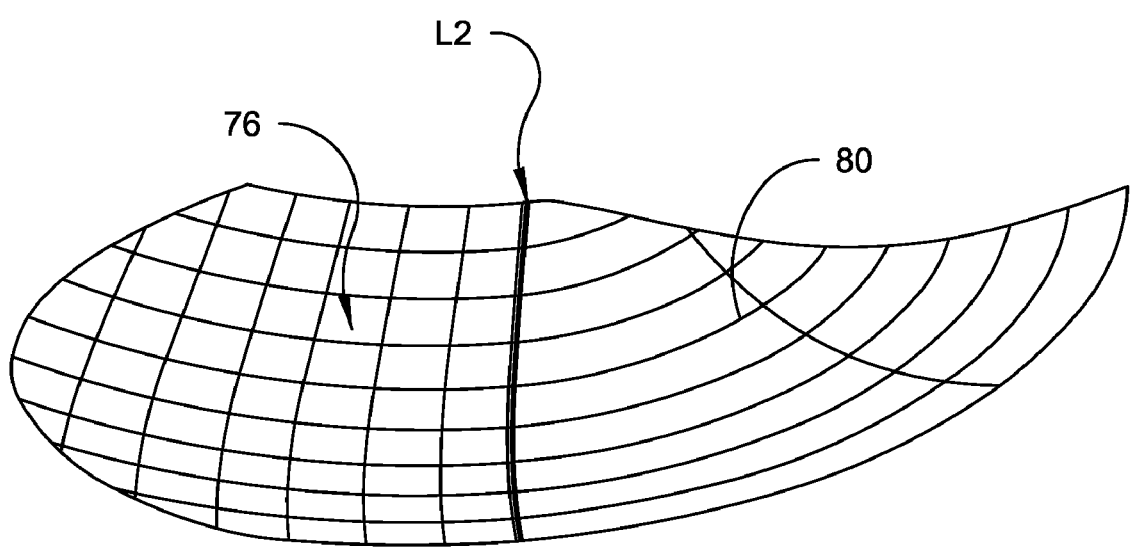
FIG. 12 is a graphical illustration of the junction between the anterior and posterior toroidal surfaces of the tibial concavities shown in FIGS. 9 and 10.

An illustration of the orientation of the toroidal sections and concavities is shown in FIG. 11, along with coordinate axes relating the sagital, coronal and transverse planes of the prosthesis. In FIG. 11, a toroidal surface of the anterior and posterior medial and lateral femoral condyles, and the anterior surfaces of the medial and lateral concavities, is represented by the first T1 and second T2 toroids, respectively. The major radius is oriented in the Y-Z or sagital plane and the major axis of rotation lies in the X-Y or coronal plane generally parallel to the X axis. A toroidal surface of the posterior medial and lateral concavities is represented by the third toroid T3. The major radius is oriented in the X-Z or transverse plane, and the major axis of rotation is oriented in the Y-Z plane generally parallel to the Y axis. An illustration of the junction at a tangent intersection L2 between the anterior 76 and posterior 78 toroidal surfaces of the medial tibial concavity 72 is shown in FIG. 12.

Figure 13:
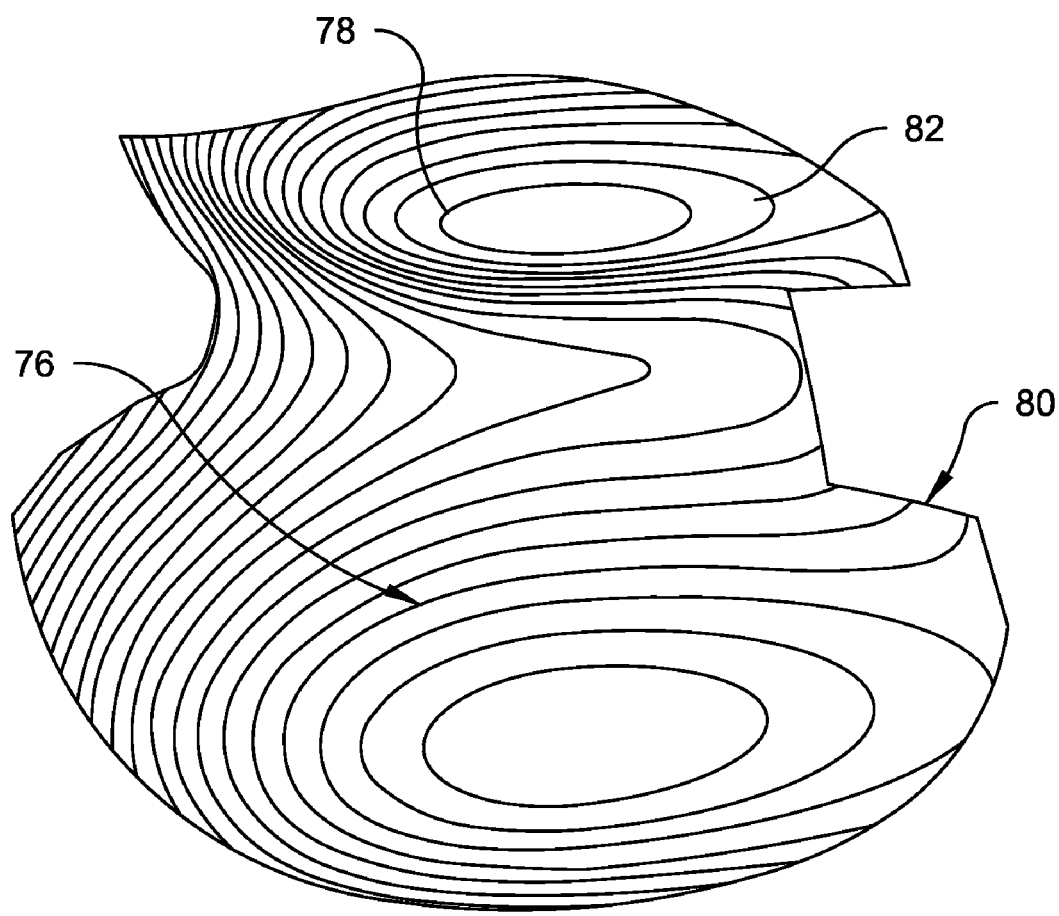
FIG. 13 is a plot illustrating with isocurves the tibial bearing surface after the anterior and posterior toroidal surfaces have been blended and a new surface patch has been fitted over the surface.

In a preferred embodiment, the anterior and posterior surfaces of the concavities are blended to transition smoothly. A plot illustrating with isocurves the tibial bearing surface after the anterior and posterior toroidal surfaces have been blended and a new surface patch has been fitted over the surface is shown in FIG. 13.

Figure 14:
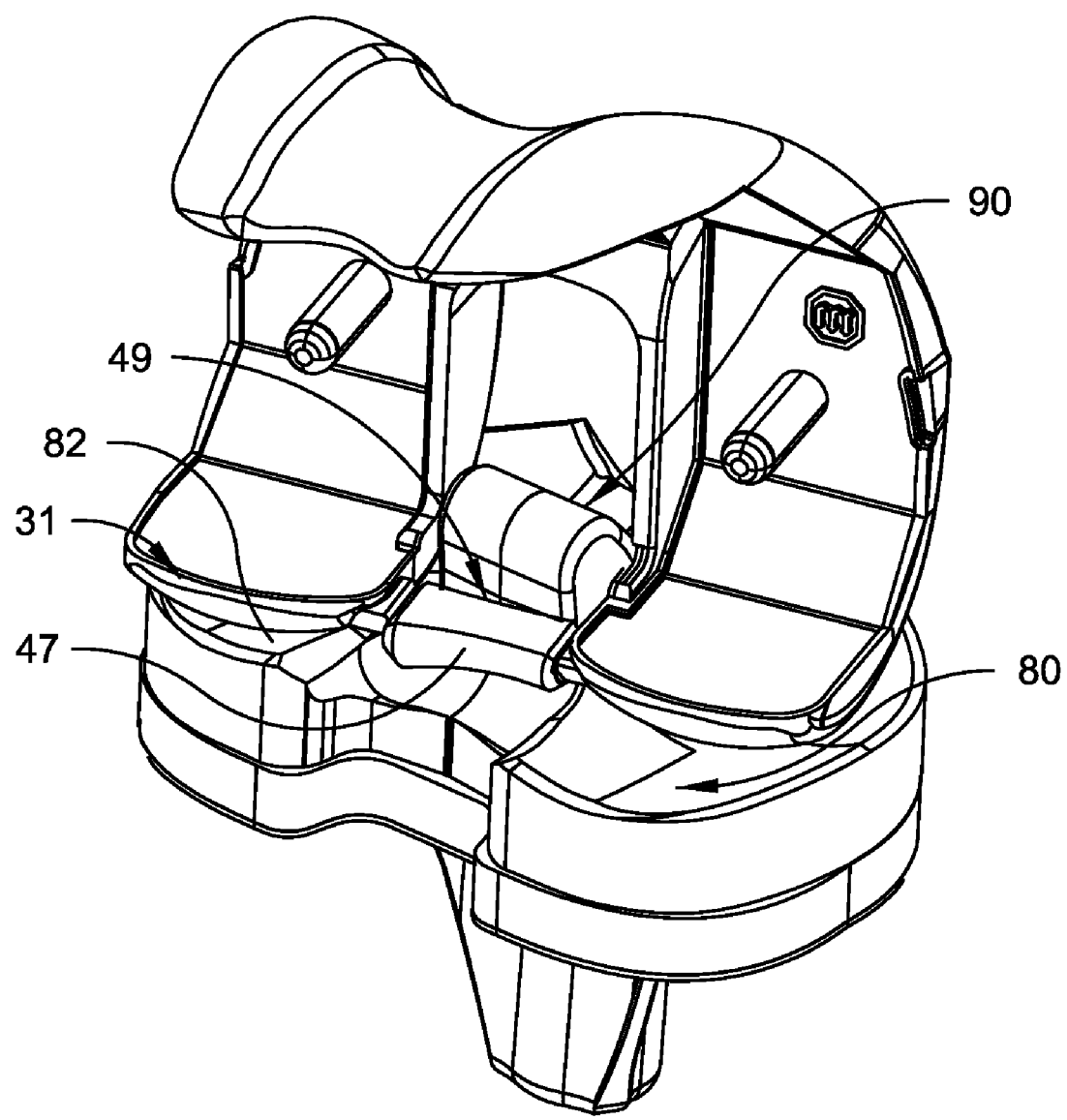
FIG. 14 is a perspective of a the knee prosthesis of FIG. 1 in 90 degrees of flexion.
Figure 15:
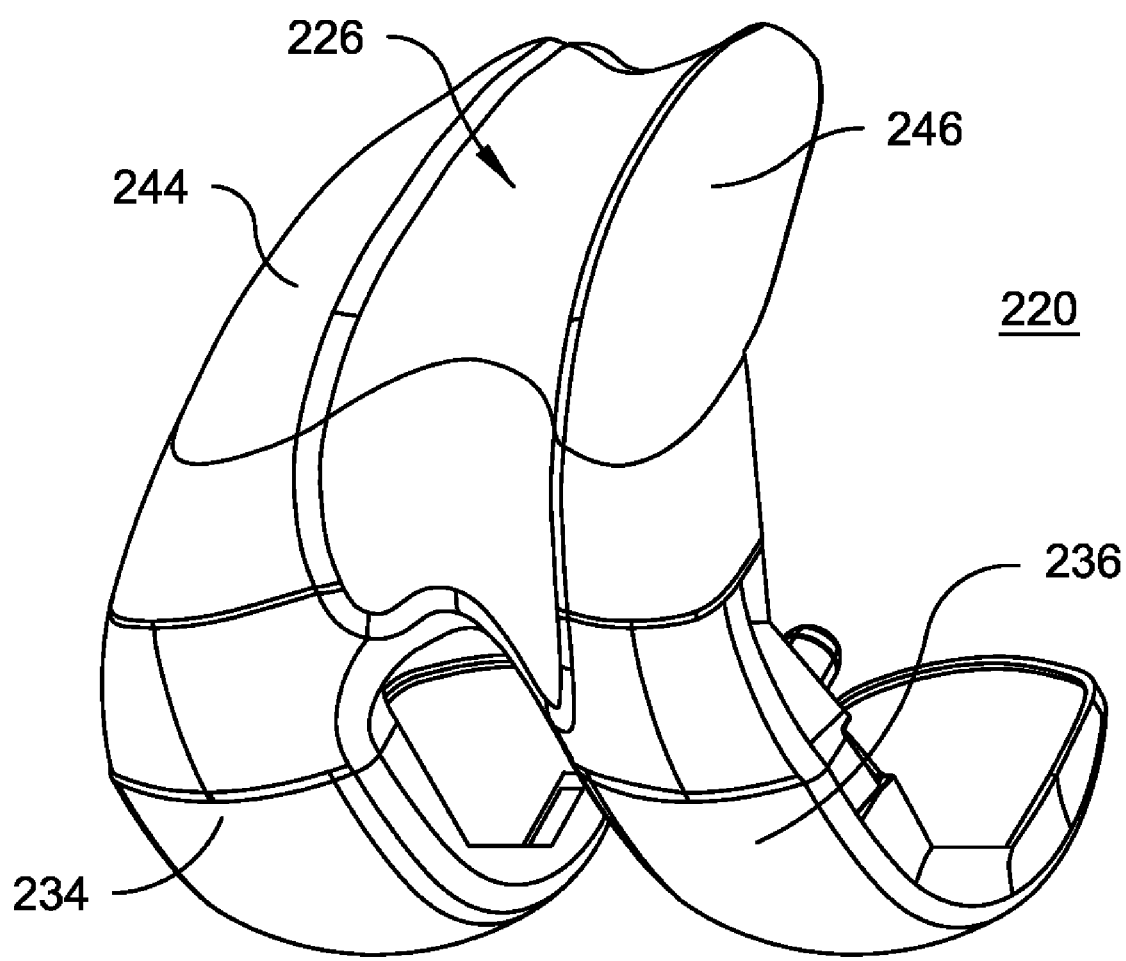
FIGS. 15 and 16 are perspectives of the femoral component in accordance with another embodiment of the invention.
Figure 16:
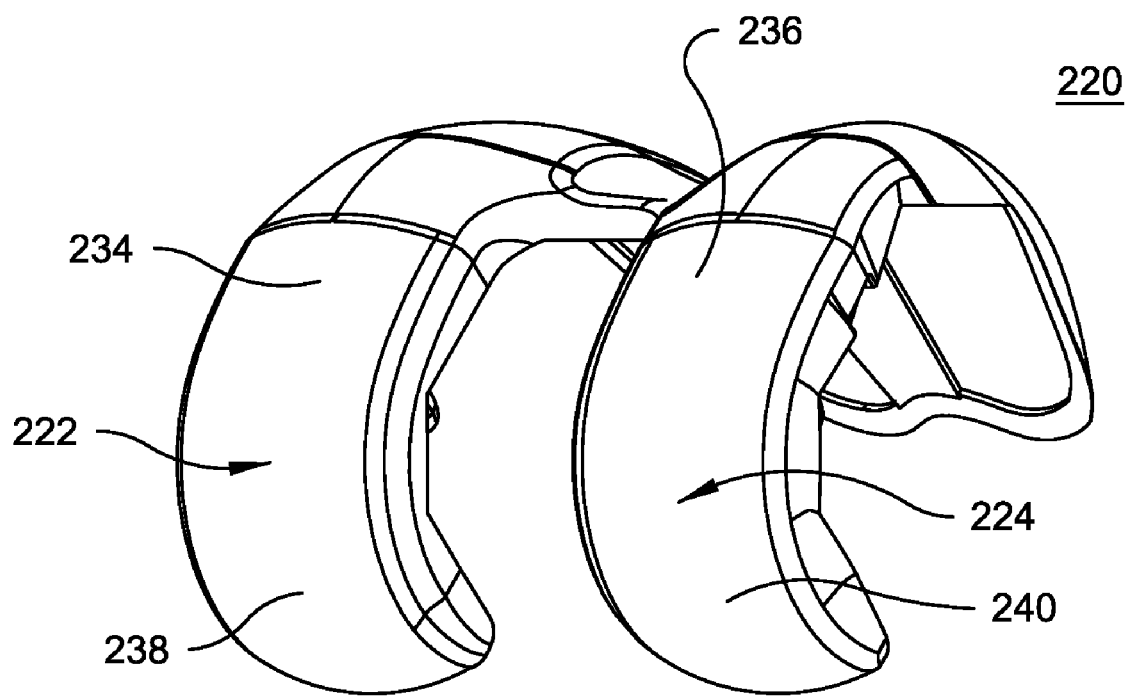
Figure 17:
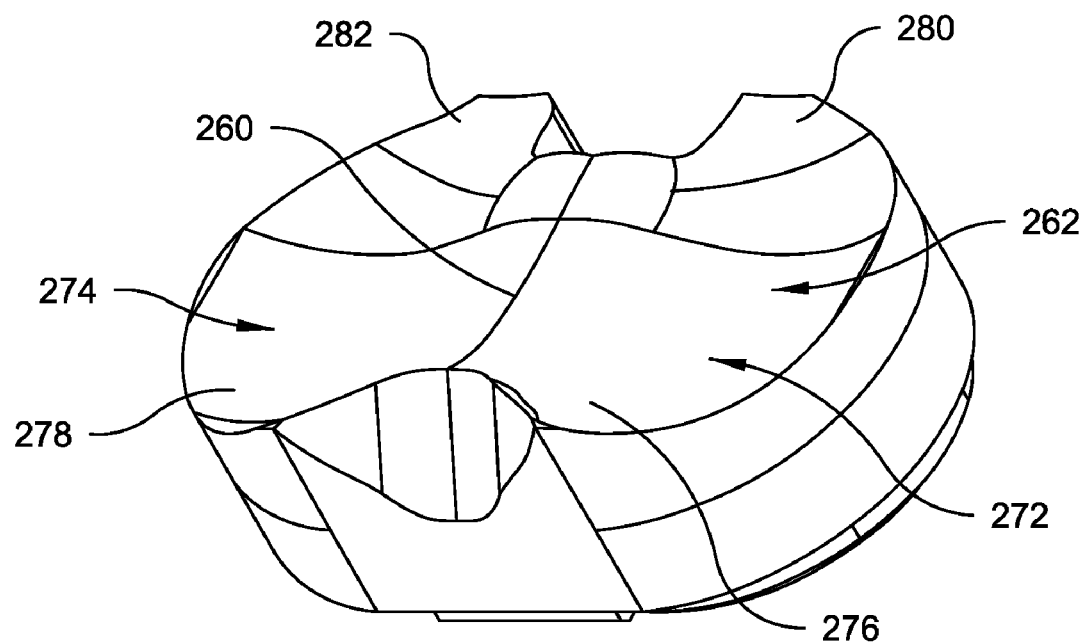
FIGS. 17 and 18 are perspectives of the tibial liner in accordance with another embodiment of the invention.
Figure 18:
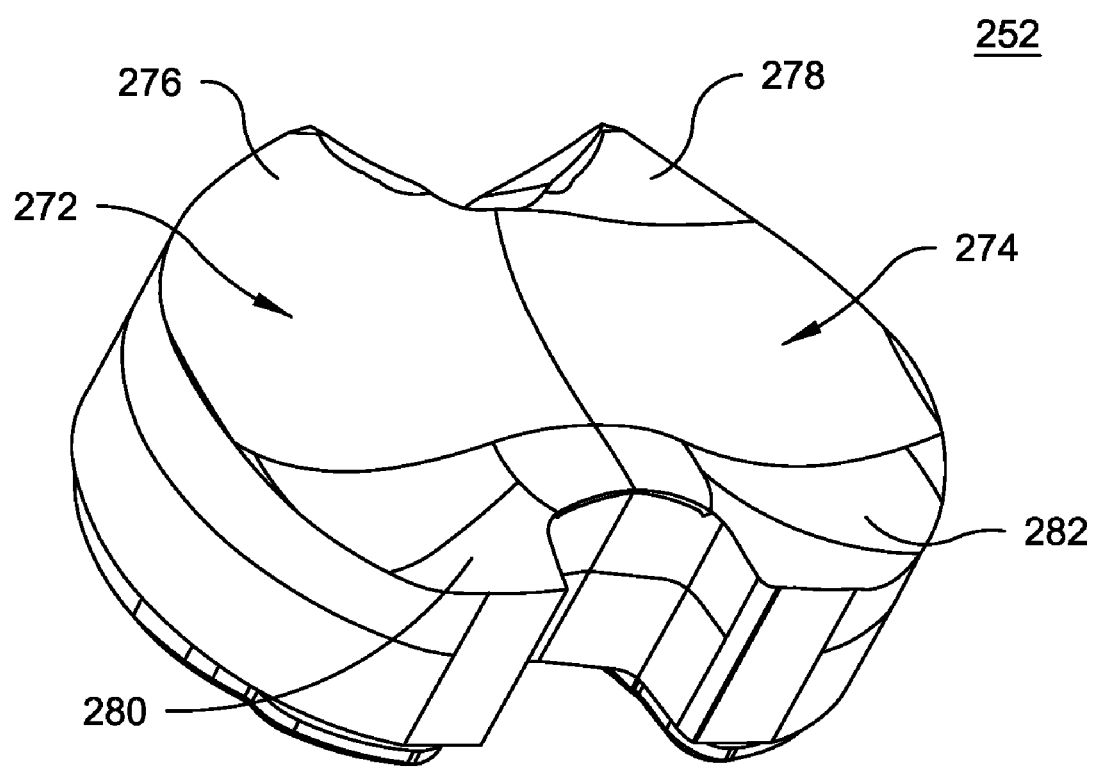
Figure 19:
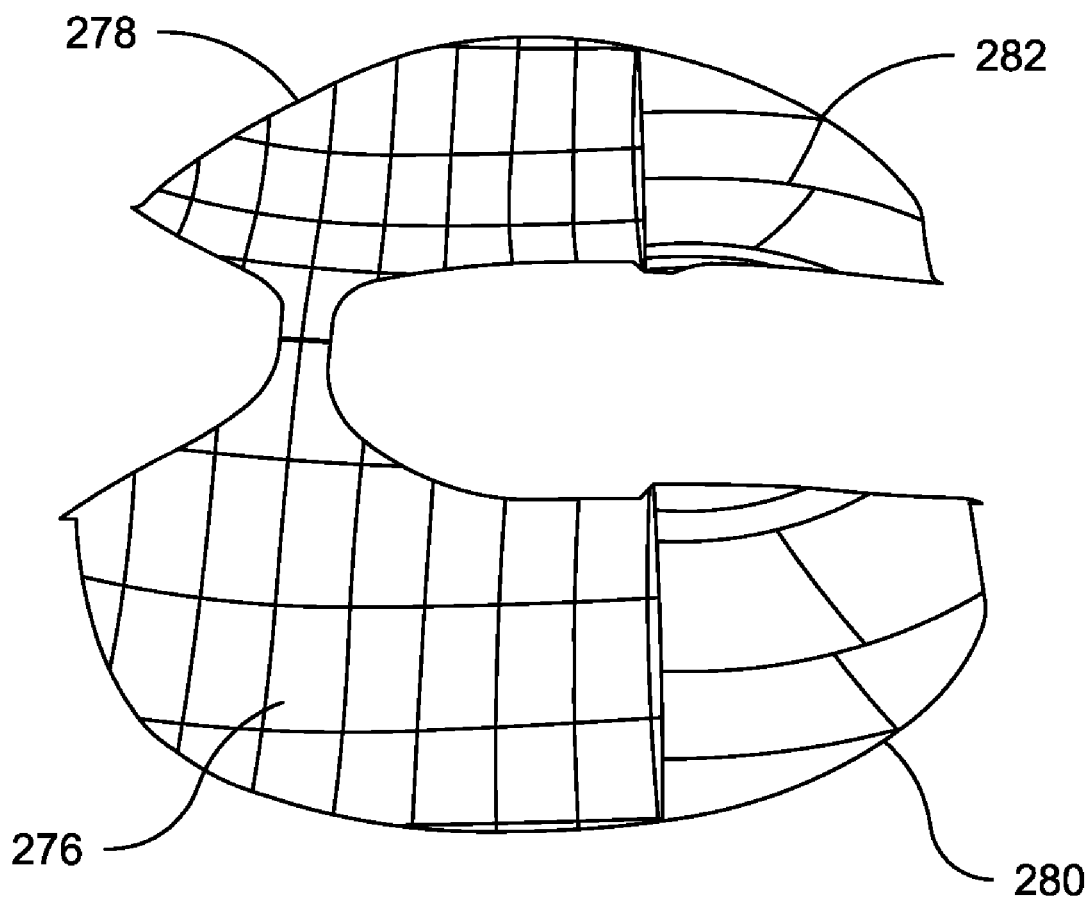
FIG. 19 is a plot illustrating with isocurves the tibial bearing surface of FIGS. 17 and 18; and, FIG. 20 is a plot illustrating with isocurves the tibial bearing surface after the anterior and posterior toroidal surfaces have been blended and a new surface patch has been fitted over the surface.
Figure 20:
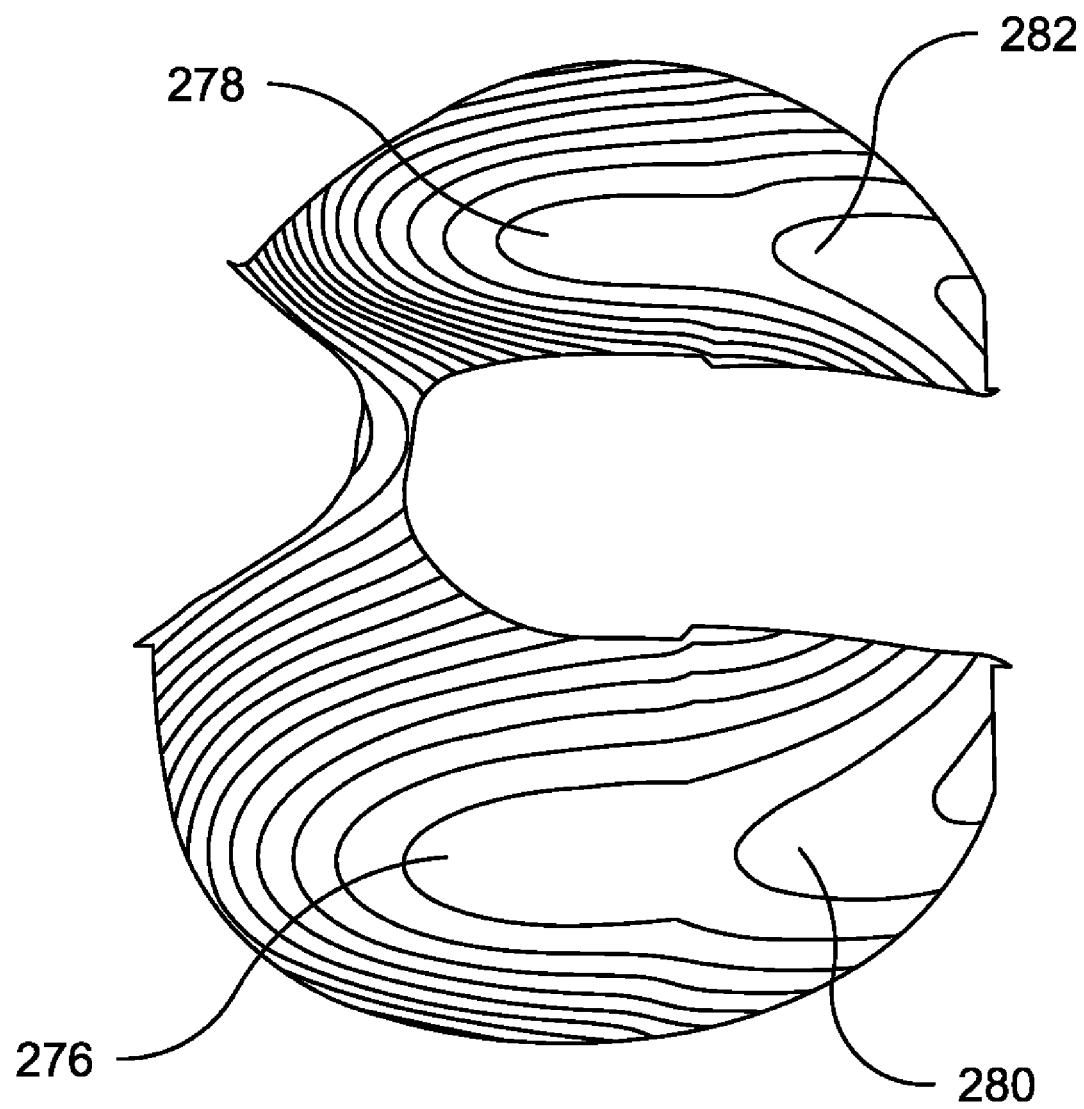

Referring to FIGS. 1 and 14, the anterior surfaces 34, 36 of the condyles 22, 24 contact the tibial component in the range of full extension to an intermediate position in partial flexion. As the knee continues to flex, the posterior surfaces 38, 40 contact the tibial component from the intermediate position to full flexion.

Furthermore, when the knee flexes, the femoral component translates posteriorly on the tibial component until the cam 47 contacts the post 90 at about 30 degrees of flexion, whereafter translation is restricted. In the embodiment illustrated in FIGS. 1-14, posterior translation of the femoral component is limited to about 1-2 millimeters. Referring to FIG. 14, the curved bearing surface 49 of the cam 47 also causes the tibia to rotate axially inwardly as the knee flexes. In a preferred embodiment, tibial rotation is greater than about 10 degrees, preferably greater than 15 degrees, more preferably up to about 20 degrees. However, the articulating surfaces and cam 47 could be designed to enable greater tibial axial rotation if desired. This complex translational and rotational movement is also enabled by the femoral condyles 22, 24 rotating in the posterior toroidal surfaces 80, 82. This embodiment of the prosthesis is used when both the anterior and posterior cruciate ligaments are surgically removed.

In addition to more accurately replicating the natural articular motion path of the human knee, the unique geometry of the articulating surfaces also reduces contact stress between the femoral condyles 22, 24 and the tibial liner 60 since the minor radius of curvature of the anterior surfaces 76, 78 of the liner is the same as the minor radius of curvature of the posterior surfaces 80, 82. Since the anterior and posterior curvature is the same, the condyles transition smoothly from front to back and do not exert excess stress on the liner 60.

To enhance deep flexion, the radius of curvature in the sagital plane of the condyles decreases rapidly near the posterior end 29, 31 of the medial 22 and lateral 24 condyles. As best seen in FIGS. 7 and 8, the posterior ends 29, 31 have very sharp radii compared to the anterior portion. The anterior sections 34, 36 blend into the posterior sections 38, 40 without abrupt transitions.

It should be readily apparent to those skilled in the art that the diameter and contour of any portion of the femoral condylar surfaces 22, 24, tibial bearing surface 62, curved cam bearing surface 49, or post 90 can be changed to alter the articular motion path of the prosthesis. For example, the major radius of curvature of the posterior surfaces of the concavities can be centered on the geometric center of the component or may be offset by a distance that gives rise to a smaller or larger posterior articulating surface. The height of the anterior 86 and posterior 88 ends of the concavities can also be varied to provide different amounts of anterior or posterior stability. The location of the deepest portion of the concavities 72, 74 can be placed anywhere on the tibial component 52 to alter the resting position of the femoral component under weight bearing load. The shape of any of the individual surfaces can be altered as desired depending on the surgeon's preference and the patient's anatomy to control the motion path of the knee.

The embodiment of the invention described above is designed for use when the anterior and posterior cruciate ligaments are surgically removed. In another embodiment shown in FIGS. 15-20, the prosthesis is designed for use when the posterior cruciate ligament is retained. In this embodiment, posterior displacement of the femur on the tibia is controlled by the posterior cruciate ligament and the toroidal surfaces are shaped such that there is no restriction to tibial axial rotation as the knee is flexed.

In the embodiment shown in FIGS. 15-20, the femoral component 220 has a similar construction to the femoral component 20 described with reference to FIGS. 1-14. The femoral component 220 includes medial 222 and lateral 224 condyles, having anterior surfaces 234, 236, and posterior surfaces 238, 240 and a patellar flange 226 with a patellar groove 242 and adjacent trochlear surfaces 244, 246. However, in this embodiment, the femoral component does not include a cam bridging the posterior ends of the condyles 222, 224. Compared to the first femoral component 20, the patellar groove 242 is deeper and the condyles 244, 246 are shallower in the coronal plane.

Likewise, the tibial component 252 has a similar construction to the tibial component 52 described with reference to FIGS. 1-14. The tibial component 252 includes a bearing liner 260 having a proximal bearing surface 262 with medial 272 and lateral 274 concavities, which engage the medial 222 and lateral 224 condyles of the femoral component 220 as the components articulate relative to one another. The concavities have toroidal anterior 276, 278 and posterior 280, 282 surfaces. However, in this embodiment, the center 261 of the liner 260 does not include a central post, but is elevated gradually to provide medial-lateral stability.

Compared to the embodiment shown in FIGS. 1-14, the concavities 272, 274 are more elevated anteriorly to prevent forward sliding of the femur during flexion. The deepest portion of the concavities is shifted posteriorly and has elevations anteriorly and laterally to allow the femoral component to translate posteriorly and the tibial component to rotate axially as the prosthesis is flexed. In this embodiment, the intact posterior cruciate ligament controls posterior femoral displacement and internal tibial rotation. The articulating surfaces are designed to avoid interference with the motion path dictated by the posterior cruciate ligament. The entire bearing surface 262 is less conforming to the condyles 222, 224 than in the first embodiment designed for posterior cruciate substitution.

The femoral component and tibial component may be constructed in various manners and from various materials. For example, the femoral component and the tibial platform may be machined, cast, forged or otherwise constructed as a one-piece integral unit from a medical grade, physiologically acceptable metal such as cobalt chromium alloy, stainless steel, titanium, titanium alloy or nickel cobalt alloy.

The tibial liner may also be constructed in various manners and from various materials. For example, the tibial liner may be machined, molded or otherwise constructed as a one-piece, integral unit out of a medical grade, physiologically acceptable polymeric materials such as any polyolefin, including high-density polyethylene, low-density polyethylene, linear-low-density polyethylene, ultra-high molecular weight polyethylene (UHMWPE), or mixtures thereof. Polymeric materials, as used herein, also include polyethylene of various forms, for example, resin powder, flakes, particles, powder, or a mixture thereof, or a consolidated form derived from any of the above. Ultra-high molecular weight polyethylene (UHMWPE) refers to linear, non-branched chains of ethylene having initial average molecular weights in excess of about 500,000, preferably above about 1,000,000, and more preferably above about 2,000,000. Often the molecular weights can reach about 8,000,000 or more. The material can be treated, for example, by radiation, chemistry, or other technology to alter its wear properties and/or strength or hardness. Initial average molecular weight means the average molecular weight of the UHMWPE starting material, prior to any irradiation.

The invention claimed is:

1. A knee replacement prosthesis having anterior, posterior, lateral, medial, distal and proximal sides and sagital, coronal and transverse planes, comprising:
  a) a femoral component that connects to the distal end of a resected femur, said femoral component including medial and lateral condyles having distal, articulating surfaces with a toroidal anterior surface and a toroidal posterior surface with major and minor axes of rotation, and a patellar flange having an articulating patellar surface; and,
  b) a tibial component that connects to the proximal end of a resected tibia, said tibial component including a proximal medial and lateral bearing surfaces that articulate with said medial and lateral condyles, respectively, said bearing surfaces having a toroidal anterior surface and a toroidal posterior surface with major radii of curvature that are oriented in different planes;
  wherein said prosthesis enables anterior-posterior translation of the femur relative to the tibia and enables the tibia to rotate about its longitudinal axis during flexion of the knee.

2. The prosthesis recited in claim 1, wherein tibial axial rotation is limited to less than about 10 degrees as the knee flexes from full extension to an intermediate position, and tibial axial rotation greater than 10 degrees is enabled as the knee flexes from the intermediate position to full flexion.

3. The prosthesis recited in claim 2, wherein the tibia rotates axially less than 10 degrees from full extension to the intermediate position, and more than 10 degrees from the intermediate position to full flexion.

4. The prosthesis recited in claim 1, wherein the major radius of curvature of each of the condylar anterior surface and the condylar posterior surface is oriented in the sagital plane, and the minor radius of curvature of each surface is oriented generally in the coronal plane.

5. The prosthesis recited in claim 1, wherein the major radii of curvature of the anterior surface and posterior surface of each condyle are unequal, and the minor radii of curvature of the surfaces are equal.

6. The prosthesis recited in claim 5, wherein the major radii of curvature of the anterior and posterior surfaces of each tibial bearing surface are unequal and the minor radii of curvature are equal.

7. The prosthesis recited in claim 6, wherein the minor radius of curvature of the condylar surfaces is equal to or smaller than the minor radius of curvature of the anterior and posterior surfaces of the tibial bearing surfaces.

8. The prosthesis recited in claim 1, wherein the major radius of curvature of the anterior surface of each tibial bearing surface is oriented in the sagittal plane, and the minor radius of curvature is oriented substantially in the coronal or transverse plane.

9. The prosthesis recited in claim 8, wherein the major radius of curvature of the posterior surface of each tibial bearing surface is oriented in the transverse plane, and the minor radius of curvature is oriented substantially in the coronal plane.

10. The prosthesis recited in claim 1, wherein each of the anterior surfaces of the medial and lateral condyles has a different major radius of curvature, and each of the posterior surfaces of the medial and lateral condyles has a different major radius of curvature.

11. The prosthesis recited in claim 10, wherein each of the anterior and posterior surfaces of the medial and lateral condyles has the same minor radius of curvature.

12. The prosthesis recited in claim 10, wherein each of the anterior surfaces of the medial and lateral tibial bearing surfaces has a different major radius of curvature, and each of the posterior surfaces of the medial and lateral tibial bearing surfaces has a different major radius of curvature.

13. The prosthesis recited in claim 12, wherein said prosthesis is constructed and arranged so that the major radius of curvature of each condylar surface is centered on the axis joining the medial and lateral epicondyles of the femur when said femoral component is connected to the femur.

14. The prosthesis recited in claim 1, wherein the medial and lateral tibial bearing surfaces share a single center for the major radius of curvature.

15. The prosthesis recited in claim 1, wherein the medial and lateral tibial bearing surfaces have a different center for the major radius of curvature.

16. The prosthesis recited in claim 1, wherein each of the anterior surfaces of said condyles has at least a first major radius of curvature in the sagital plane and each of the posterior surfaces has at least a first major radius of curvature in sagital plane that is smaller than the first anterior radius of curvature.

17. The prosthesis recited in claim 16, wherein each of the condylar anterior surfaces and posterior surfaces has multiple major radii of curvature in the sagital plane.

18. The prosthesis recited in claim 17, wherein each of the anterior and posterior surfaces has the same minor radius of curvature.

19. The prosthesis recited in claim 1, wherein each of the anterior surfaces of said tibial bearing surfaces has at least a first major radius of curvature-in the sagital plane and at least a first major radius of curvature in the transverse plane that is larger than the first anterior radius of curvature.

20. The prosthesis recited in claim 19, wherein each of anterior surfaces of said tibial bearing surfaces has multiple major radii of curvature in the sagital plane and each of the posterior surfaces has multiple major radii of curvature in the transverse plane.

21. The prosthesis recited in claim 20, wherein each of the anterior and posterior surfaces of said tibial bearing surfaces has the same minor radius of curvature.

22. The prosthesis recited in claim 1, wherein the condyles translate posteriorly in the tibial bearing surfaces during flexion and anteriorly during extension.

23. The prosthesis recited in claim 22, wherein posterior translation is about 1-2 millimeters after the prosthesis is fully flexed.

24. The prosthesis recited in claim 1, wherein the posterior portion of each condyle is shaped to allow flexion greater than 100 degrees.

25. The prosthesis recited in claim 1, wherein the posterior portion of each condyle is shaped to allow flexion greater than 130 degrees.

26. The prosthesis recited in claim 1, wherein said tibial component comprises a base having distal and proximal surfaces, and a liner having a distal surface that engages the proximal surface of the base and a proximal surface forming said bearing surfaces that engages and articulates with the femoral component.

27. The prosthesis recited in claim 26, wherein said base comprises a base plate that rests on the tibial plateau, and a keel fixed to the distal surface of the base plate that can be inserted into the proximal tibial medullary canal.

28. The prosthesis recited in claim 27, wherein the distal surface of said plate has a textured, roughened surface.

29. The prosthesis recited in claim 1, wherein said prosthesis is constructed and arranged to engage the posterior cruciate ligament so that anterior and posterior translation of the femoral component relative to the tibial component is controlled by the patient's posterior cruciate ligament.

30. The prosthesis recited in claim 29, wherein contact between the cam and post occurs at knee flexion greater than about 30 degrees.

31. The prosthesis recited in claim 1, wherein said prosthesis is constructed and arranged to engage the posterior cruciate ligament so that tibial rotation is controlled by the patient's posterior cruciate ligament.

32. The prosthesis recited in claim 1, wherein said femoral component includes a cam connecting the posterior ends of the condyles, and said tibial component includes a central post intermediate said concavities.

33. The prosthesis recited in claim 32, wherein anterior and posterior translation of the femoral component relative to the tibial component is controlled by said cam and central post.

34. The prosthesis recited in claim 32, wherein rotation of the tibia about its longitudinal axis is controlled by said cam and central post.

35. The prosthesis recited in claim 1, wherein said prosthesis is constructed and arranged so that the major radius of curvature of each condylar surface is centered on the axis joining the medial and lateral epicondyles of the femur when said femoral component is connected to the femur.

36. The prosthesis recited in claim 1, wherein the anterior and posterior surfaces of each tibial bearing surface are blended smoothly together.

37. The prosthesis recited in claim 36, wherein said tibial bearing surfaces are fitted with a patch surface that articulates with said condyles.

38. A knee replacement prosthesis having anterior, posterior, lateral, medial, distal and proximal sides and sagital, coronal and transverse planes, comprising:
   a) a femoral component that connects to the distal end of a resected femur, said femoral component including medial and lateral condyles having a distal, articulating surfaces with a toroidal anterior surface and a toroidal posterior surface with different major and minor axes of rotation, and a patellar flange having an articulating patellar surface; and,
   b) a tibial component that connects to the proximal end of a resected tibia, said tibial component including a proximal bearing surface with medial and lateral concavities that articulate with said medial and lateral condyles, said concavities having a toroidal anterior surface and a toroidal posterior surface with different major and minor radii of curvature;
   wherein said prosthesis enables anterior-posterior translation of the femur relative to the tibia and enables the tibia to rotate about its longitudinal axis during flexion of the knee.

* * * * *